United States Patent [19]

Lensky

[11] Patent Number: 5,606,064
[45] Date of Patent: Feb. 25, 1997

[54] PROCESS FOR THE PREPARATION OF BENZYL-PIPERIDYLMETHYL-INDANONES

[75] Inventor: Stephen Lensky, Kürten, Germany

[73] Assignee: Bayer Aktiengesellschaft, Leverkusen, Germany

[21] Appl. No.: 552,330

[22] Filed: Nov. 2, 1995

[30] Foreign Application Priority Data

Nov. 8, 1994 [DE] Germany .......................... 44 39 822.0

[51] Int. Cl.$^6$ .................................................. C07D 211/02
[52] U.S. Cl. .......................................... 546/185; 546/206
[58] Field of Search ..................................... 546/185, 206

[56] References Cited

U.S. PATENT DOCUMENTS 4,069,222  1/1978  Horgan et al. ..................... 260/293.52
4,191,828  3/1980  Horgan et al. ......................... 546/185

FOREIGN PATENT DOCUMENTS 0296560  12/1988  European Pat. Off. .
0535496   4/1993  European Pat. Off. .
0421670   1/1992  Japan .

OTHER PUBLICATIONS

Esmann, M. et al., Anal. Biochem. 189: 274–282, 1990, Chemical Abstracts: 114: 19958 (1991).
Patent Abstracts of Japan vol. 16, No. 180, abstract of JP 04–21,670 (1992).

*Primary Examiner*—C. Warren Ivy
*Assistant Examiner*—Charanjit S. Awlakh
*Attorney, Agent, or Firm*—Sprung Horn Kramer & Woods

[57] ABSTRACT

The invention relates to a new process for the preparation of benzyl-piperidylmethyl-indanones known as medicaments, which is characterized in that the appropriately substituted pyridinium salts are hydrogenated.

6 Claims, No Drawings

PROCESS FOR THE PREPARATION OF BENZYL-PIPERIDYLMETHYL-INDANONES

The present invention relates to a process for the preparation of benzyl-piperidylmethyl-indanones. Benzyl-piperidylmethyl-indanones are active compounds for the treatment of CNS disorders.

EP 296 560 has already described a process for the synthesis of benzyl-piperidylmethyl-indanones, 1-benzyl-4-piperidones being reacted in a four-stage process to give the desired final product.

The yields of the first three stages are in each case less than 65% of theory. Moreover, this synthesis requires the use of organolithium compounds and working under an inert gas atmosphere.

A three-stage process starting from pyridine-4-aldehyde and various indanones has now been described in EP 535 496. In this process the 2-(pyridin-4-ylmethyl)-ylideneindanones are hydrogenated to give piperidines and subsequently hydrogenated. This process requires more complicated purification processes (chromatography+ crystallization) and therefore inevitably leads to poorer yields (max. up to 29%).

A process for the preparation of benzyl-piperidylmethyl-indanones of the general formula (I)

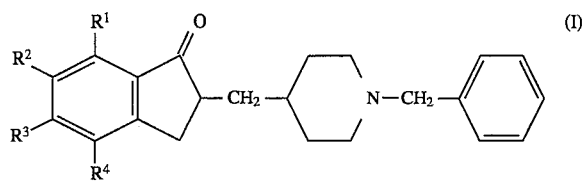

in which

R$^1$, R$^2$, R$^3$ and R$^4$ are identical or different and represent hydrogen or represent straight-chain or branched alkyl, alkoxy or alkoxycarbonyl having up to 6 carbon atoms, alkyl- or dialkyl-(C$_1$–C$_6$)-aminocarbonyloxy or halogen, has now been found, which is characterized in that pyridinium salts of the formula (II)

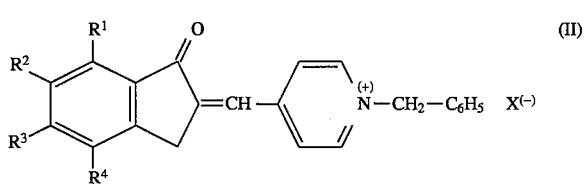

in which

R$^1$, R$^2$, R$^3$ and R$^4$ have the meaning indicated and

X$^{\ominus}$ represents an anion of the series chloride, bromide, iodide, tosylate, sulphate, are hydrogenated with hydrogen in the presence of a hydrogenation catalyst, if appropriate in an inert solvent.

Surprisingly, it is possible with the aid of the process according to the invention to obtain the benzyl-piperidylmethyl-indanones by direct hydrogenation at normal pressure of the pyridinium salts. In this one-stage synthesis, the final products are obtained in unexpectedly high yields, in particular with respect to the processes known from the prior art, which afford poor yields and require higher pressures.

Preferably, compounds of the formula (I) are prepared by the process according to the invention in which R$^1$ to R$^4$ represent hydrogen or R$^1$ and R$^4$ represent hydrogen, and R$^2$ and R$^3$, if appropriate independently of one another, represent methoxy, methylaminocarbonyloxy, dimethylaminocarbonyloxy or halogen.

Suitable solvents are, if appropriate, independently of one another the customary inert solvents which do not change under the reaction conditions. These preferably include ethers, such as diethyl ether, dibutyl ether, methyl tert-butyl ether, dioxane or tetrahydrofuran, alcohols such as methanol, ethanol, propanol, isopropanol or butanol, chlorinated hydrocarbons such as dichloromethane, trichloromethane, tetrachloromethane or dichloroethylene, acetone, acetonitrile, dimethylformamide, dimethyl sulphoxide, N-methylpyrrolidone or tetramethylurea; hydrocarbons such as hexane, toluene, benzene or xylene can also be used. Moreover, it is possible to employ the solvents mentioned as mixtures with one another and also as mixtures with water. Alcohols, in particular methanol or ethanol, are particularly preferred.

The hydrogenation catalysts used are the customary hydrogenation catalysts known in organic chemistry. These in particular include platinum and also platinum compounds, palladium, palladium on carbon, Raney nickel, ruthenium and also ruthenium compounds, if appropriate on support materials such as active carbon or silica. Platinum and platinum compounds and ruthenium and ruthenium compounds are preferred. Platinum dioxide (Adams hydrogenation catalyst) is very particularly preferably used.

The reaction is in general carried out in a temperature range from –20° to +120° C., preferably from 0° to +80° C., very particularly preferably from +10° to +35° C.

The hydrogenation can be carded out at normal pressure, but also at elevated pressure. In general, it is carried out in a pressure range from 1 to 100 atmospheres, preferably a hydrogen pressure from 1 to 20 atmospheres.

When carrying out the hydrogenation, about 0.01 to 200 g, preferably 1 to 30 g, of the catalyst to be used are employed relative to 100 g of pyridinium salt of the formula (II).

The pyridinium salts of the general formula (II) are new and are prepared by reacting pyridines of the general formula (III)

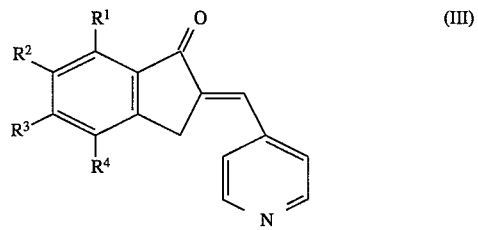

in which

R$^1$, R$^2$, R$^3$ and R$^4$ have the meaning indicated, if appropriate in the presence of an inert solvent, with compounds of the general formula (IV)

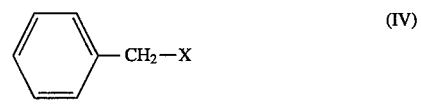

in which

X represents a customary leaving group from the halogen series, preferably chlorine or bromine, if appropriate in the presence of a catalyst.

The inert solvents used in this case are preferably the customary organic solvents which do not change in the reaction. These preferably include ethers such as diethyl ether, dibutyl ether, methyl tert-butyl ether, dioxane or tetrahydrofuran, chlorinated hydrocarbons such as dichloromethane, trichloromethane or tetrachloromethane, acetone, acetonitrile, dimethylformamide, dimethyl sulphoxide, alcohols such as methanol, ethanol, propanol or isopropanol or N-methylpyrrolidone, sulpholane or tetramethylurea. The solvents mentioned can also be employed in the form of mixtures.

Acetonitrile, acetone, butanone, dimethylformamide, N-methylpyrrolidone, tetramethylurea and DMSO are particularly preferred.

Suitable catalysts are alkali metal iodides and tosylates. Potassium iodide and sodium iodide are preferred.

The reaction to give the pyridinium salts can be carried out either with cooling, at room temperature or with heating. It is preferably carried out at the boiling point of the solvent employed or at 75°–100° C.

In the reaction, the pyridine of the general formula (III) is in general dissolved in the respective solvent at boiling heat and the benzyl compound of the formula (IV) is added. Customarily, the product precipitates in pure form or can be crystallized completely after cooling. After filtering off and washing the precipitate with an inert solvent, the product can be directly processed further.

EXPERIMENTAL SECTION

Example 1

2-(Pyridin-4-yl)-methylene-indan-1-one:

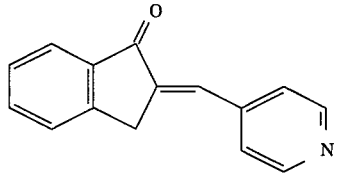

13.2 g of indanone, 15 g of pyridine-4-aldehyde and 19 g of p-toluenesulphonic acid were heated to boiling under reflux in a water separator for 5 h in 250 ml of toluene. The resulting precipitate was filtered off with suction after cooling and stirred at room temperature for 30 rain in 10% sodium carbonate solution. The resulting, pale-yellow precipitate was filtered off with suction, washed with water and dried in air. Yield: 19.3 g (87%)

Example 2

5,6-Dimethoxy-2-(pyridin-4-yl)-methylene-indan-1-one:

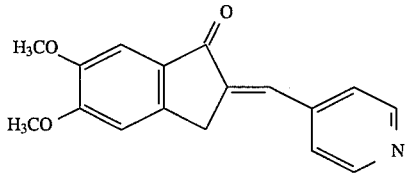

19.2 g of 5,6-dimethoxyindanone, 15 g of pyridine-4-aldehyde and 19 g of p-toluenesulphonic acid were heated to boiling under reflux in a water separator for 5 h in 250 ml of toluene. The resulting precipitate was filtered off with suction after cooling and stirred at room temperature for 30 min in 10% strength sodium carbonate solution. The resulting pale-yellow precipitate was filtered off with suction, washed with water and dried in air. Yield: 24.4 g (87%).

Example 3

1-Benzyl-4-(indan-1-on-2-ylidene)-methyl-pyridinium bromide:

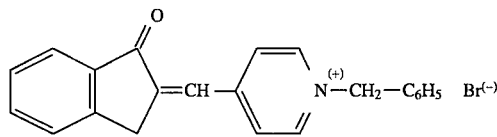

10 g of compound from Example 1 were dissolved in 150 ml of boiling acetonitrile and 7.5 g of benzyl bromide were added hot. The mixture was heated to boiling under reflux for a further 2 h, the product precipitating. It was allowed to cool, and the resulting precipitate was filtered off with suction, washed with acetonitrile and methyl tert-butyl ether in the sequence indicated and dried in air.
Yield: 14.75 g (83%).

Example 4

1-Benzyl-4-(5,6-dimethoxyindan-1-on-2-ylidene)-methyl-pyridinium bromide

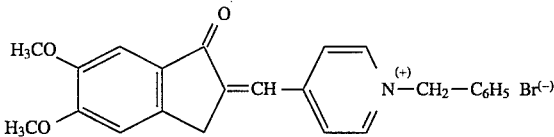

10 g of compound from Example 2 were dissolved in 500 ml of boiling acetonitrile and 7.5 g of benzyl bromide were added hot. The mixture was heated to boiling under reflux for a further 2 h, the product precipitating. It was allowed to cool, and the resulting precipitate was filtered off with suction, washed with acetonitrile and methyl tert-butyl ether in the sequence indicated and dried in air.
Yield: 14 g (83%).

Example 5

1-Benzyl-4-(indan-1-on-2-yl)-methyl-piperidine 10 g of compound from Example 3 and 1 g of platinum dioxide (Adams hydrogenation catalyst) were suspended in 50 ml of methanol. The mixture was then hydrogenated at normal pressure and at room temperature for 24 h. The catalyst was then filtered off and the filtrate was concentrated. The residue was taken up using 5% sodium hydrogen carbonate solution and the resulting precipitate was filtered off with suction, washed with water and dried in vacuo.
Yield: 6.6 g (81%).

Example 6

1-Benzyl-4-(5,6-dimethoxyindan-1-on-2-yl)-methyl-piperidine:

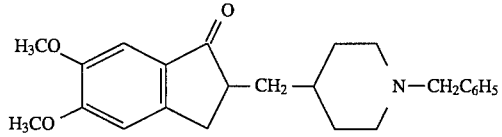

10 g of compound from Example 4 and 1 g of platinum dioxide (Adams hydrogenation catalyst) were suspended in 50 ml of methanol. The mixture was then hydrogenated at normal pressure and at room temperature for 24 h. The catalyst was then filtered off and the filtrate was concentrated. The residue was taken up using 5% sodium hydrogen carbonate solution, and the solution was extracted 3 times with dichloromethane, dried and concentrated.

Yield: 6.9 g (81%).

I claim:

1. Process for the preparation of benzyl-piperidylmethyl-indanones of the general formula

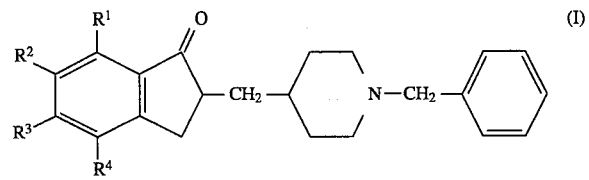

in which $R^1$, $R^2$, $R^3$ and $R^4$ are identical or different and represent hydrogen or represent straight-chain or branched alkyl, alkoxy or alkoxycarbonyl having up to 6 carbon atoms, alkyl- or dialkyl-$(C_1-C_6)$-aminocarbonyloxy or halogen, characterized in that pyridinium salts of the formula (II)

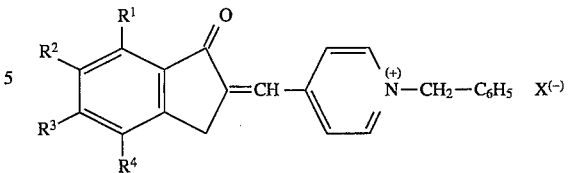

in which $R^1$, $R^2$, $R^3$ and $R^4$ have the meaning indicated and $X^\ominus$ represents an anion of the series chloride, bromide, iodide, tosylate, sulphate, are hydrogenated with hydrogen in the presence of a hydrogenation catalyst, if appropriate in an inert solvent.

2. Process according to claim 1 for the preparation of compounds of the general formula (I), wherein $R^1$ to $R^4$ represent hydrogen.

3. Process according to claim 1 for the preparation of compounds of the general formula (I), wherein $R^1$ and $R^4$ represent hydrogen and $R^2$ and $R^3$ represent methoxy.

4. Process according to claim 1 characterized in that the hydrogenation catalyst employed is platinum or its compounds.

5. Process according to claim 1 characterized in that the hydrogenation is carried out at a pressure from 1 to 20 atmospheres using hydrogen.

6. Process according to claim 1 characterized in that it is carried out in a temperature range from −20° to +120° C.

* * * * *